United States Patent [19]

Bae

[11] 4,020,330
[45] Apr. 26, 1977

[54] DENSITOMETER

[75] Inventor: Hyung Du Bae, Brea, Calif.

[73] Assignee: International Telephone and Telegraph Corporation, New York, N.Y.

[22] Filed: May 3, 1976

[21] Appl. No.: 682,494

[52] U.S. Cl. .................. 235/151.3; 235/151.34; 235/156; 73/32 R
[51] Int. Cl.² .................. G01F 15/02; G06F 7/38
[58] Field of Search .......... 235/151.3, 151.34, 156; 73/30, 32, 194 M

[56] References Cited

UNITED STATES PATENTS

| | | | |
|---|---|---|---|
| 3,862,405 | 1/1975 | Beck | 235/151.34 |
| 3,875,955 | 4/1975 | Gallatin et al. | 235/151.34 X |
| 3,878,374 | 4/1975 | Schlatter | 235/151.34 X |
| 3,934,127 | 1/1976 | Schlatter et al. | 235/151.34 |

Primary Examiner—Edward J. Wise
Attorney, Agent, or Firm—A. Donald Stolzy

[57] ABSTRACT

A vibration densitometer which can be calibrated to an accuracy never before possible, i.e. to within an error of 0.25 percent or less, and in two fluids or gases or gas mixtures, one, both or none being an elemental fluid or gas. The fluids or gases or fluid or gas mixtures have different density equations $$d_i = A_i T_i^2 - i\, B_i$$
$$d_j = A_j T_j^2 - B_j$$

the first of which is converted by $\Delta T_i$, an extremely linear function of container or pipeline pressure, such that $$d_j = A_i(T_i - \Delta T_i)^2 - B_i.$$

where
$d_i$ and $d_j$ are the two respective fluid densities, $T_i$ and $T_j$ are two periods directly proportional to the reciprocals of the respective vibration frequencies, and $A_i$, $A_j$, $B_i$ and $B_j$ are constants.

It was heretofore unknown to calibrate a vibration densitometer in two fluids or gases or fluid or gas mixtures with the aforesaid extremely small error.

4 Claims, 11 Drawing Figures

| POINT | PERIOD ($T_i$) (Millisecond) | $d_j$ | $d_i$ | $\Delta d_i = d_i - d_j$ |
|---|---|---|---|---|
| 1 | .504330 | .7608 | .745347 | −.015450 |
| 2 | .506916 | .9565 | .9380157 | −.018484 |
| 3 | .514023 | 1.4996 | 1.472593 | −.027004 |
| 4 | .529031 | 2.6713 | 2.6225925 | −.045370 |

FIG.6.

| POINT | $P_i$ | $(P_i)^2$ | $\Delta T_i$ (Microseconds) | $(P_i)(\Delta T_i)$ |
|---|---|---|---|---|
| 1 | 252 | $(252)^2$ | −207.89 | −(252)(207.89) |
| 2 | 314 | $(314)^2$ | −247.45 | −(314)(247.45) |
| 3 | 491 | $(491)^2$ | −356.52 | −(491)(356.52) |
| 4 | 852 | $(852)^2$ | −58.20 | −(852)(58.20) |
| $\Sigma$ | $\sum_{i=1}^{4} P_i$ | $\sum_{i=1}^{4} (P_i)^2$ | $\sum_{i=1}^{4} \Delta T_i$ | $\sum_{i=1}^{4} (P_i)(\Delta T_i)$ |

| $P_i$ | $T_i$ | $\Delta T_i$ | $T_{ai}$ | $d_j$ | $d_i$ | D |
|---|---|---|---|---|---|---|
| 252 | .504330 | −.0002081 | .5045381 | .7608 | .7608 | 0 |
| 314 | .506916 | −.0002467 | .5071627 | .9565 | .9565 | 0 |
| 491 | .514023 | −.0003570 | .514380 | 1.4996 | 1.4996 | 0 |
| 852 | .529031 | −.0005818 | .5296128 | 2.6713 | 2.6713 | 0 |

DENSITOMETER

BACKGROUND OF THE INVENTION

This invention relates to instruments for producing an output which is a function of the densities of two elemental fluids or gases, one elemental fluid or gas and one fluid or gas mixture, or two fluid or gas mixtures, and more particularly to a highly accurate vibration densitometer.

In the past it has been impossible to obtain an accurate density output from a vibration densitometer in the aforesaid two fluids, gases and fluid or gas mixtures.

SUMMARY OF THE INVENTION

In accordance with the vibration densitometer of the present invention, the two equations for two fluids or gases, respectively, are $d_i = A_i T_i^2 - B_i$
$d_j = A_j T_j^2 - B_j$ and the first equation is converted to the following $d_j = A_i(T_i - \Delta T_i)^2 - B_i$ where $\Delta T_i$ is a function of the container or pipeline pressure, and the last equation makes it possible to calibrate the invention very accurately for both fluids or gases simultaneously.

In the foregoing:

$d_i$ and $d_j$ are the two respective fluid densities, $T_i$ and $T_j$ are two periods directly proportional to the reciprocals of the respective vibration frequencies, and $A_i$, $A_j$, $B_i$ and $B_j$ are constants.

The above-described and other advantages of the present invention will be better understood from the following detailed description when considered in connection with the accompanying drawings.

BRIEF DESCRIPTION OF THE DRAWINGS

In the drawings, which are to be regarded as merely illustrative.

DESCRIPTION OF THE PREFERRED EMBODIMENT

Figure 1:
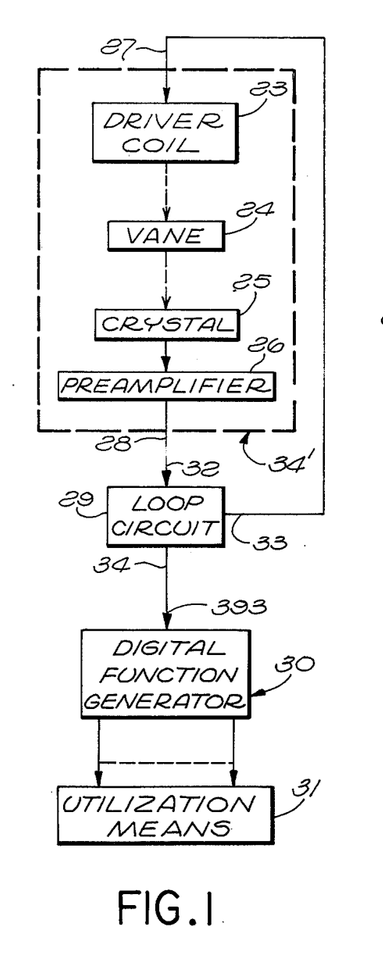
FIG. 1 is a block diagram of a densitometer constructed in accordance with the present invention.

In the drawings, in FIG. 1, a vibration densitometer probe is indicated at 34' having a driver coil 23, a vane 24, a piezoelectric crystal 25 and a preamplifier 26.

Probe 34' has an input lead 27 and an output lead 28. Other blocks shown in FIG. 1 are a loop circuit 29, a digital function generator 30 and utilization means 31. Loop circuit 29 has an input lead 32 and output leads 33 and 34. Digital function generator 30 has an input lead 393 connected from loop circuit output lead 34. The output of digital function generator 30 is connected to utilization means 31.

The output lead 28 of probe 34' is connected to the input lead 32 of loop circuit 29. The input lead 27 of probe 34' is connected from the output lead 33 of loop circuit 29. Probe 34' and loop circuit 29 form a closed loop electromechanical oscillator. Vane 24 is submerged in a fluid. The density of the fluid is a function of the frequency at which vane 24 vibrates.

Digital function generator 30 may have its input lead 393 connected from lead 33 or at other points in loop circuit 29. Loop circuit 29 impresses a square wave voltage on input lead 393 of digital function generator 30 having a mark-to-space ratio of 1:1.

Utilization means 31 shown in FIG. 1 may be a density indicator, a specific gravity indicator, a process controller or otherwise.

Reference is hereby made to certain U.S. patents. These patents are listed for convenience in the following:

1. U.S. Pat. No. 3,677,067.
2. U.S. Pat. No. 3,706,220.
3. U.S. Pat. No. 3,738,155.
4. U.S. Pat. No. 3,741,000.
5. U.S. Pat. No. 3,878,374.
6. U.S. Pat. No. 3,885,140.
7. U.S. Pat. No. 3,883,811.
8. U.S. Pat. No. 3,775,597.

The foregoing patents of paragraphs (1), (2), (3), (4), (5), (6), (7) and (8) are hereinafter referred to as patents P1, P2, P3, P4, P5, P6, P7 and P8, respectively.

Probe 34' shown in FIG. 1 may be conventional. Alternatively, probe 34' may be similar to or identical to a probe disclosed in any of the patents P1-P8.

Preamplifier 26 shown in FIG. 1 may be conventional.

All the structure shown in FIG. 1 may be identical to that shown in P5, P6 and P7 except for digital function generator 30, if desired. This common structure, side from digital function generator 30, also operates in a manner identical to that in which it operates in P5, P6 and P7.

OPERATION

In the embodiment of the invention shown in FIG. 1, probe 34' and loop circuit 29 form an electromechanical oscillator which oscillates at a frequency dependent upon the density of the fluid in which vane 24 is immersed. The same is true of the pulse repetition frequency of the square wave voltage applied to the input led 393 of digital functional generator 30.

Digital function generator 30 may be described as a digital linearization circuit. It produces a digital output directly proportional to density from the input signal thereto impressed upon the input lead 393 thereto.

Figure 2:
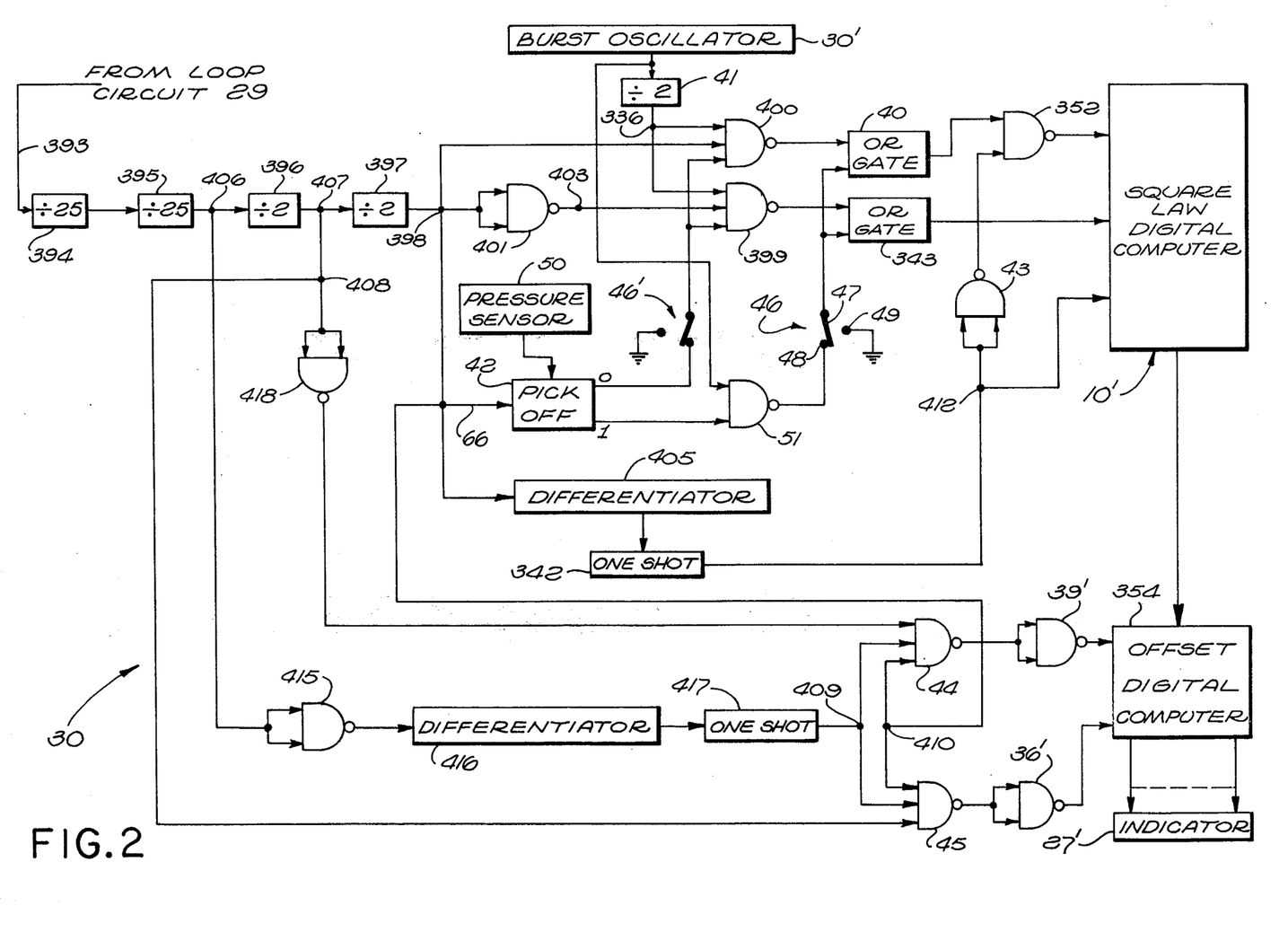
FIG. 2 is a more detailed block diagram of the digital function generator shown in FIG. 1.

The digital function generator 30 of FIG. 1 is indicated in greater detail in FIG. 2. Digital function generator 30 has input led 393. A divide-by-twenty-five divider 394, a divide-by-twenty-five divider 395, a divide-by-two divider 396 and a divide-by-two divider 397 are connected in succession from input lead 393 to a terminal junction 398.

Digital function generator 30 has a burst oscillator 30'. NAND gates are provided at 399 and 400 with their outputs connected to a square law digital computer 10'. The output of NAND gate 400 is connected to a divider 37' in the computer 10' of FIG. 3 through an OR gate 40 and a NAND gate 352. The output of NAND gate 399 is connected to a rate multiplier 38' in FIG. 3 through an OR gate 343.

NAND gate 400 receives one input from junction 398 and another input from oscillator 30' through a divide-by-two divider 41. NAND gate 399 receives one input from the output of divider 41, and another input from the output of an inverter 401 connected from junction 398. The output of inverter 401 is connected to a junction 403. One input of NAND gate 399 is connected from junction 403.

A differentiator 405 and a pick off 42 are connected from junction 398. A one shot 342 is connected from differentiator 405 to divider 37' in square law digital computer 10' to reset the same.

Digital function generator 30 shown in FIG. 2 has various other junctions 406, 407, 408, 409 and 410.

The output of one shot 342 is connected to a junction 412. Junction 412 is connected to square law digital computer 10' and to another input of NAND gate 352 through an inverter 43.

An inverter 415, a differentiator 416 and a one shot 417 are connected in succession in that order from junction 406 to junction 409. Inverters 39' and 36' are provided which receive inputs from the output of corresponding NAND gates 44 and 45, respectively, which, in turn, are connected from the output of one shot 417 by respective connections from junctions 409. Junction 406 is connected from the output of divider 395 and to the input of dividier 396. Junction 407 is connected from the output of divider 396 and to the input of divider 397. Junctions 407 and 408 are connected together. NAND gates 45 has one input connected from junction 408.

Junctions 398 and 410 are connected together. NAND gates 44 and 45 both receive an input from the output of divider 397 by respective connections from junction 398. An inverter 418 is connected from junction 407 to another input of NAND gate 44.

An offset digital computer 354 receives an input from square law digital computer 10' and from the outputs of inverters 36' and 39'. Computer 354 may be identical to the one of P5, P6 or P7 or be otherwise conventional.

An indicator 27' is connected from the output of offset digital computer 354. Offset digital computer 354 may be decimal or binary. The indicator 27' may be any simple conventional indicator with one lamp for each binary stage or a decimal indicator as described in P5, P6 and P7. Indicator 27' may be entirely conventional. Offset digital computer 354 may be conventional or of the type or identical to that illustrated in P5, P6 and P7. The same is true of square law digital computer 10' and indicator 27'.

Offset computer 354 in FIG. 2 produces a binary or a binary coded decimal (BCD) output so that indicator 27' may be read directly, binary or decimal, in density or specific gravity.

Offset digital computer 354 and indicator 27' are connected in succession in that order from square law digital computer 10'. Offset digital computer 354 may be entirely conventional or as disclosed in P8

Offset digital computer 354 receives serial groups of serial pulses from computer 10', the number of pulses in each group being directly proportional to the square of the period of the square wave appearing at terminal junction 398 and adjusted by pick off 42.

Pick off 42 shuts off NAND gates 399 and 400 at the beginning of the leading edges of pulses appearing at both junctions 398 and 403. The 0 output of pick off 42 does not go high after the said leading edges until a period $\Delta T_i$ (to be defined) has passed. If $\Delta T_i$ is negative, a switch 46 is maintained in the closed position shown. Switch 46 has a pole 47, and two contacts 48 and 49. When $\Delta T_i$ is positive, pole 47 is held into engagement with contact 49, which is connected to ground, and a switch 46' is closed, as shown in FIG. 2.

A pressure sensor 50 from the pipeline has an output that is impressed upon pick off 42 also. The 1 output of pick off 42 is connected to inputs of NAND gates 399 and 400. The 0 output of pick off 42 with the output of burst oscillator 30' are impressed as inputs on a NAND gate 51, the output of which can be or not be, as desired, connected to an input of each of the OR gates 40 and 343.

The said square is likewise directly proportional to the square of the period of the square wave appearing on input lead 393.

Figure 3:
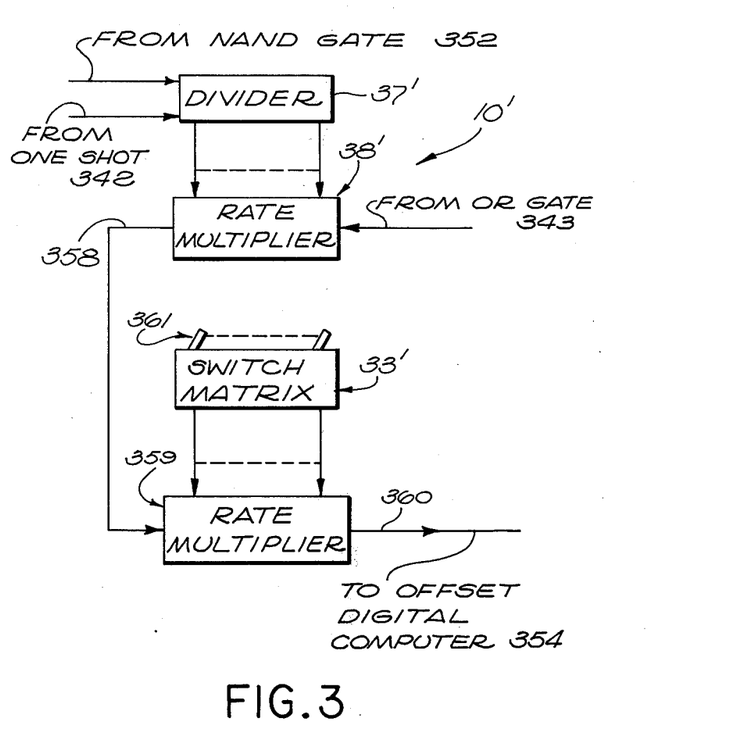
FIG. 3 is a more detailed block diagram of a square law digital computer shown in FIG. 2.

Square law digital computer 10' is illustrated in FIG. 3 and may be identical to the structure and operation of that disclosed in P5, P6 and P7 or otherwise conventional. The square law computer 10' shown in FIG. 3 has a divider 37' which is merely a counter that counts the output pulses from NAND gate 352. Differentiator 405 and one shot 342 set the count of divider 37' to zero upon the leading edge of the pulse appearing at junction 403 (FIG. 2) and shown at E6 in FIG. 11.

Figures 10, 11:
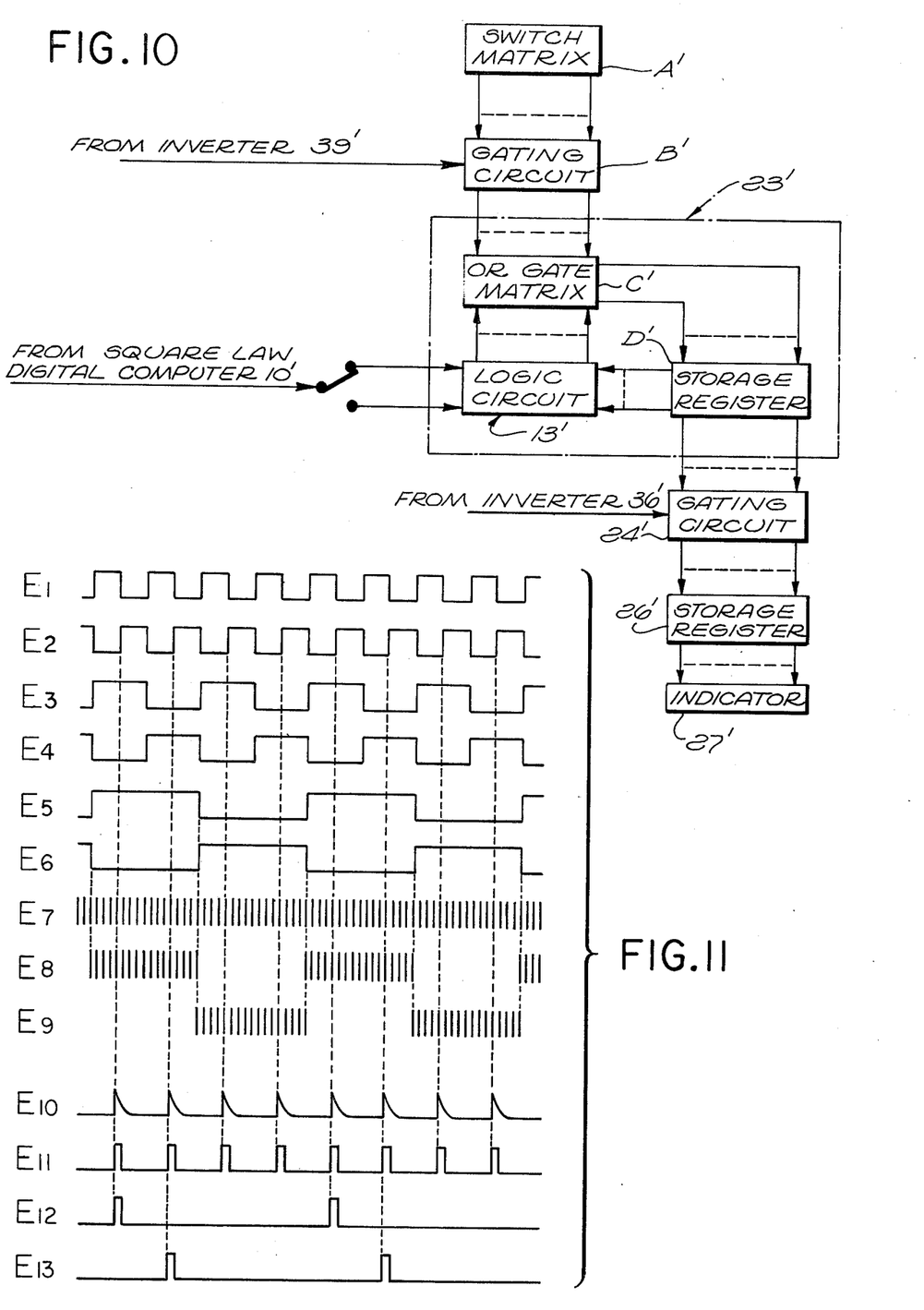
FIG. 10 is a block diagram of the conventional offset digital computer shown in FIG. 2.
FIG. 11 is a graph of another group of waveforms characteristic of the operation of the present invention.

A rate multiplier 38' is connected from OR gate 343 and produces on its output lead 358 a number of serial pulses in a group which is a fraction of the total input pulses in a group such as a group shown at E8 in FIG. 11 (methane only) dependent upon the number stored in the register of the counter of divider 37'. The output pulses in a group on output lead 358 of rate multiplier 38' is then directly proportional to the square of the period of the square wave either at junction 398 in FIG. 2 or at input lead 393 therein.

In FIG. 3, a switch matrix 33' is connected to a rate multiplier 359. Rate multiplier 359 is also connected from rate multiplier ouput lead 358 to offset digital computer 354. Switch matrix 33' has a set of manual operators 361 to produce binary or decimal switch settings. Binary switches may be employed. Alternatively, binary coded decimal (BDC) switches may be employed. The number of pulses in a group on the output lead 360 of rate multiplier 359 is less than the input thereto, in part, depending upon the setting of the switch matrix 33'.

In FIG. 3, the counter of divider 37' may be entirely conventional. As stated previously, switch matrix 33' may also be entirely conventional. The same is true of rate multiplier 38' and 359.

Typically, the square wave appearing at junction 398 in FIG. 2 has a period of about 0.5 second. Typically, the pulse repetition frequency of the output signal of burst oscillator 30' in FIG. 2 is 1.0 megahertz. Further, typically, the number of pulses in each of the groups at E8 and E9 in FIG. 11 are about 125,000.

The pulses in each grouping at E8 go to rate multiplier 38' in FIG. 3. The pulses in each group E9 go to divider 37' in FIG. 3.

Figure 4:
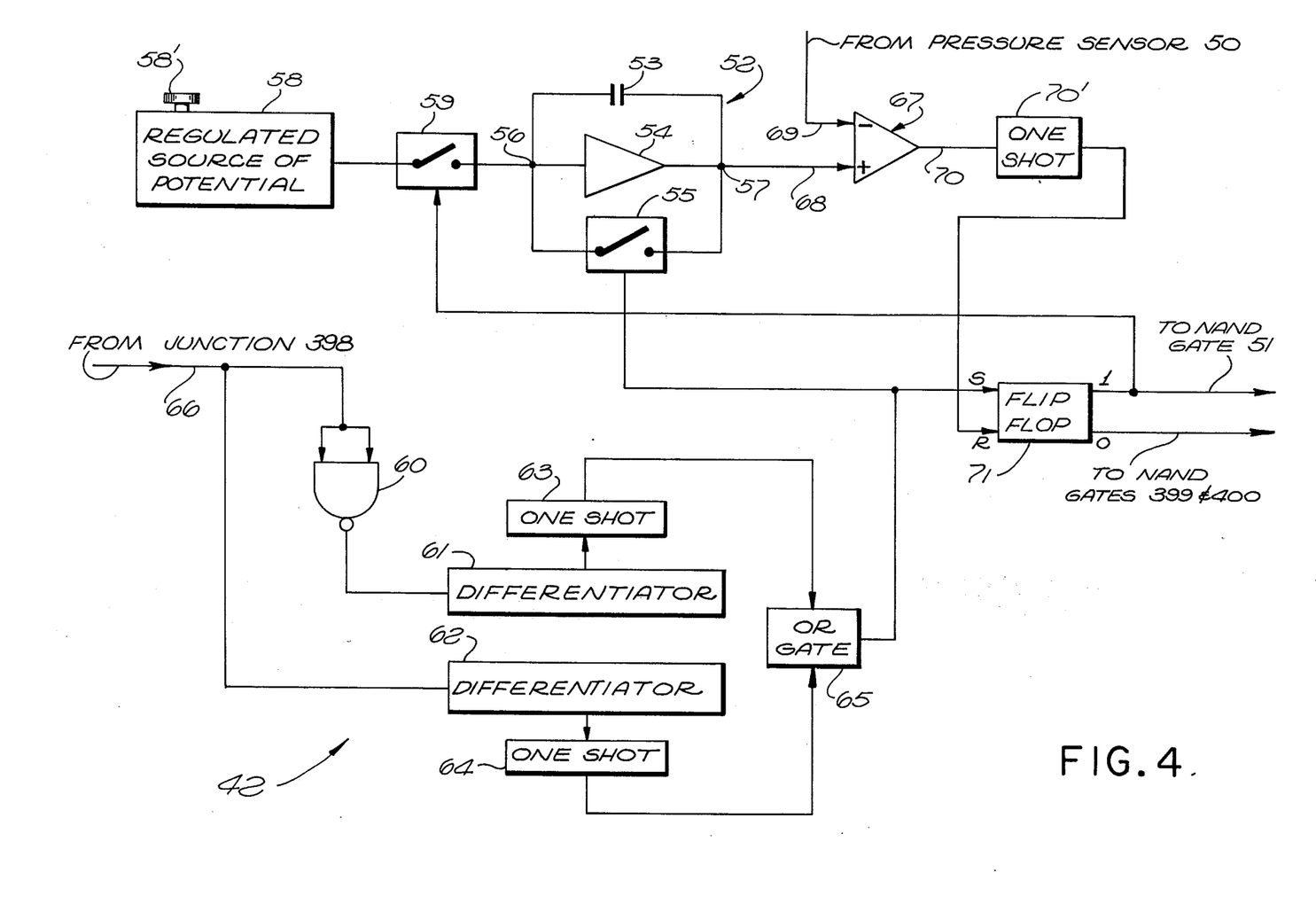
FIG. 4 is a more detail block diagram of a pick off shown in FIG. 2.

A more detailed block diagram of pick off 42 (FIG. 2) is illustrated in FIG 4 including a conventional integrator 52 having a capacitor 53, an amplifier 54 and a reset switch 55. Integrator 52 has input and output junctions 56 and 57, respectively. A regulated source of potential 58 is connected to input junction 56 via an input switch 59 and a resistor 56'. Source 58 may be adjustable at 58', if desired.

Reset switch 55 is operated at the leading and trailing edges of the square wave appearing at junction 398 in FIG. 2 through an inverter 60, differentiators 61 and 62, one shots 63 and 64, and an OR gate 65.

Pick off 42 thus has an input lead 66 connected from junction 398 in FIG. 2.

Pick off 42 has a differential amplifier 67 with non-inverting and inverting input leads 68 and 69, respectively, and an output lead 70.

A flip-flop is provided at 71. A one shot 70' is connected from lead 70 to the reset input of flip flop 71. The output of OR gate 65 is connected to the set input of flip flop 71.

The 1 output of flip flop 71 controls input switch 59 and is also connected to NAND gate 51 in FIG. 2. The 0 output of flip flop 71 is connectable to NAND gates 399 and 400 through switch 46' in FIG. 2.

Lead 69 is FIG. 4 is connected from pressure sensor 50 in FIG. 2.

When $\Delta T_i$ is always positive, in FIG. 2 NAND gate 51, switch 46, and OR gate 40 and 343 may be omitted. When $\Delta T_i$ is always negative, nothing is omitted.

Figure 5:
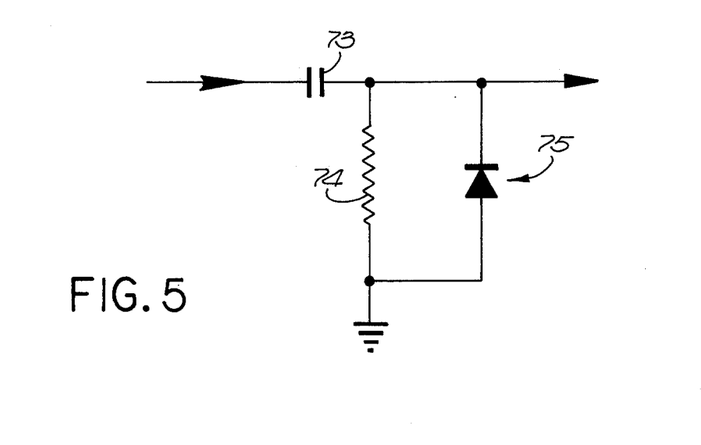
FIG. 5 is a schematic diagram of a differentiator.

All of the differentiators disclosed herein may be of the type shown in FIG. 5 including a capacitor 73, a resistor 74 and a diode 75.

In FIG. 2 the phrase "pressure sensor" is hereby defined for use herein and for use in the claims as including conventional signal conditioning electronics which are disclosed in a number of older U.S. patents, and which are disclosed, at least in part, as a linear variable displacement transformer (LVDT) in the later U.S. Pat. No. 3,853,006. The output of pressure sensor 50 is thus a D.C. voltage produced by the said conventional means which is included in the definition "pressure sensor."

Figure 9:
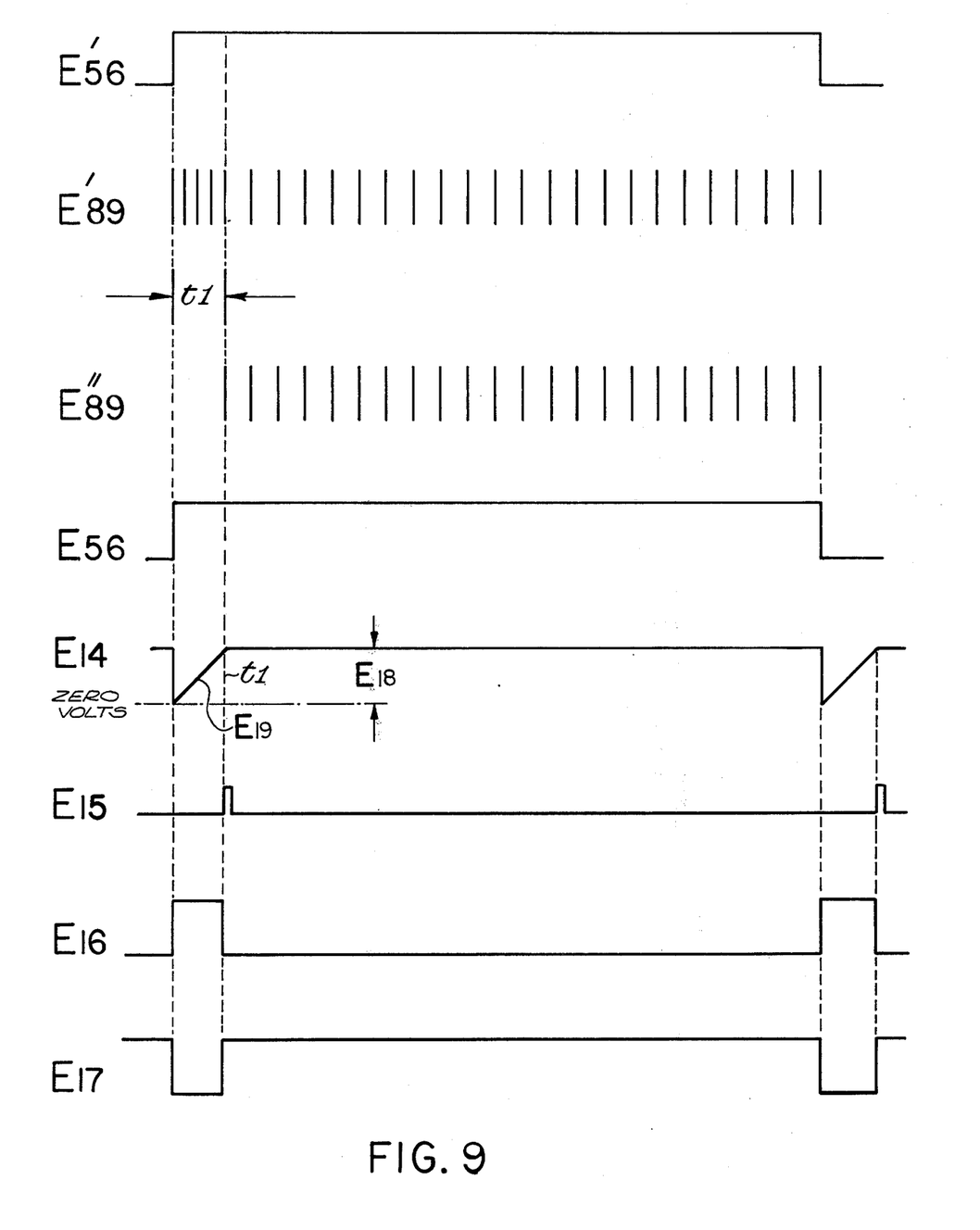
FIG. 9 is a graph of a group of waveforms characteristic of the operation of the present invention.

In FIG. 9, waveform E'56 is shown twice for clarity. The waveforms of FIGS. 9 and 11 relate to nitrogen and methane density measurements, respectively. It is, however, substantially impossible to show waveforms graphically to scale because $\Delta T_i$ is such a small period. Waveforms are thus not necessarily shown graphically to scale anywhere in the drawings hereof.

If the 1 output of pick off 42 were always maintained low, and the 0 output thereof were always maintained high, the waveforms of FIG. 11 would always occur. However, there is a $\Delta T_i$ compensation to be described (it is used for nitrogen only).

The vane 24 in FIG. 1 vibrates in a gas at a resonant frequency so that output on lead 34 of loop circuit 29 is a square wave as described herein of a pulse repetition frequency (PRF) equal to the said resonant frequency. The mark-to-space ratio of this and the other square waves referred to herein is always unity. The variable T may be defined as $$T = 1/f \tag{1}$$

where $f$ is the pulse repetition frequency of the signal appearing at junction 398 in FIG. 2.

As has been recently discovered, e.g. see U.S. Pat. No. 3,677,067, $$d = AT^2 - B \tag{2}$$

where

A may be a positive or negative constant, B may be a positive or negative constant, and $d$ is the density of the gas in which vane 24 is immersed (often in a pipeline of flowing gas). Both of the constants A and B in (2) are usually positive in (2).

Densitometers of the type disclosed in all the patents cited herein have been accurate to within 0.5 percent or better. However, a need exists for even greater accuracy. Moreover, if the said prior art densitometers are calibrated in one gas and used in another, a second calibration is frequently required, which second calibration practically is impossible in the field without the expenditure of considerable time and expense. This problem effectively cannot be solved by the customer or user because the calibration process requires considerable training and the same is again time-consuming and expensive.

It is an industry standard that the densitometer of the present invention be tested in nitrogen gas and used in a gas different from nitrogen (the gas with which the densitometer of the present invention is actually to be used).

The present invention is constructed as follows. The constants A and B are preferably determined empirically by the conventional method of least squares or least squares method (LSM). However, this is done for both nitrogen and methane, for example, because the A and B for each are different.

$$d_i = A_i T_i^2 = B_i \tag{3}$$

and $$d_j = A_j T_j^2 - B_j \tag{4}$$

where $d_i$ and $d_j$ are the densities of nitrogen and, for example, methane, respectively, $A_i$ and $A_j$ are the A constants for nitrogen and methane, respectively, $T_i$ and $T_j$ are the periods corresponding to nitrogen and methane, respectively, and $B_i$ and $B_j$ are the B constants for nitrogen and methane, respectively.

Measure $d_i$ and $T_i$ for $m$ points and curve fit by the LSM as follows by adding all columns except that of $T_i$.

| Point | $d_i$ | $T_i$ | $T_i^2$ | $T_i^4$ | $d_i T_i^2$ |
|---|---|---|---|---|---|
| 1 | . | . | . | . | . |
| 2 | . | . | . | . | . |
| 3 | . | . | . | . | . |
| . | . | . | . | . | . |
| . | . | . | . | . | . |
| $m$ | . | . | . | . | . |
| | $\sum_{i=1}^{m} d_i$ | | $\sum_{i=1}^{m} (T_i)^2$ | $\sum_{i=1}^{m} (T_i)^4$ | $\sum_{i=1}^{m} (d_i)(T_i)^2$ |

All equations obtained by the LSM herein may be so obtained with any number of points, as desired.

Solve the following simultaneous equations (5) and (6) for $A_i$ and $B_i$.

$$mB_i + A_i \sum_{i=1}^{m} (T_i)^2 = \sum_{i=1}^{m} d_i \tag{5}$$

$$B_i \sum_{i=1}^{m} (T_i)^2 + A_i \sum_{i=1}^{m} (T_i)^4 = \sum_{i=1}^{m} (d_i)(T_i)^2 \tag{6}$$

Find $A_j$ and $B_j$ in the same manner, if desired, for further calibration steps or checking.

Then find, by measurement or computation from (3) and (4), with all constants determined, $\Delta T_i$ where $$d_j = A_i (T_i - \Delta T_i)^2 - B_i \qquad 7$$

and $$d_j = A_j T_j^2 - B_j \qquad 8$$

Notice in (7) that the subscript of $d$ is $j$, whereas all of the other subscripts are $i$.

If the first derivative of $d_i$ with respect to $T_i$ in (3) is $d_i'$, then $$d_i' = \frac{dd_i}{dT_i} \qquad (9)$$

and $$d_i' = 2A_i T_i \qquad (10)$$

or $$\frac{dd_i}{dT_i} = 2A_i T_i \qquad (11)$$

The differential equation which follows then results.

$$dd_i = 2A_i T_i dT_i \qquad 12$$

If the differentials of (12) are not infinitesimals, but still very small, viz. (it has been discovered that they are very small), $$\Delta d_i \cong dd_i$$

and $\Delta T_i \cong dT_i$ $$\Delta d_i = 2A_i T_i \Delta T_i \qquad 13$$

Solving (13) for $\Delta T_i$, $$\Delta T_i = \frac{\Delta d_i}{2A_i T_i} \qquad (14)$$

A more accurate equation for $\Delta T_i$ is $$\Delta T_i = [T_i] \left[ 1 \pm \sqrt{1 - \frac{\Delta d_i}{d_i + B_i}} \right] \qquad (15)$$

where $\Delta d_i / d_i + B_i$ is not small in comparison to unity.

The terms $\Delta d_i$ and $\Delta T_i$ may be either positive or negative.

If the customer checks the nitrogen calibration pressure sensor 50 must be connected. Switches 46 and 46' in FIG. 2 are then put into the positions shown. This adds pulses passed by NAND gate 51 directly proportional to $-\Delta T_i$ (in the case of methane, $\Delta d_i$ and $\Delta T_i$ are both negative) less those which would have been supplied by NAND gates 399 and 400. Operators 361 are set to $A_i$ in FIG. 3 and matrix $A'$ in FIG. 10 is set to $B_i$.

For calibration or a commercial run of methane the connection of the pressure sensor 50 of FIG. 2 to a calibration container or pipeline is omitted, and operators 361 in FIG. 3 are set to $A_j$ while matrix $A'$ in FIG. 10 is set to $B_j$. To switch to methane, both switches 46 and 46' are moved to the positions thereof other than as shown. Switches 46 and 46' may be ganged, if desired.

If a standardized densitometer is not required and $\Delta T_i$ is always to be positive, OR gates 40 and 343, switch 46 and NAND gate 51 may be omitted. The position of switch 46' then determines whether the use is in nitrogen or methane. The algebraic sign of $\Delta T_i$ will always be known in advance.

When $\Delta T_i$ is positive, and no structure is removed from FIG. 2, the pole of switch 46 is always ground.

Any gas or gas mixture may be substituted for the nitrogen gas and/or methane gas so long as the mixture does not have components which vary greatly during operation.

The use of pressure sensor 50 shown in FIG. 2 will now become evident. It has been discovered that $\Delta T_i$ is an extremely linear function of container or pipeline pressure. Thus, $$\Delta T_i = K_a + K_b P_i \qquad 16$$

where $K_a$ and $K_b$ are constants, and $P_i$ is the container or pipeline pressure of the nitrogen.

The constants $K_a$ and $K_b$ are preferably determined empirically and by the use of the LSM as follows. The term, $\Delta d_i$, as defined below $$\Delta d_i = d_i = d_j \qquad 17$$

is determined at one period only, then another, and so on for any number of points. These determinations, with all other constants known, may be made by the use of equations (3) and (4) or by measuring $d_i$ and $d_j$ for each of a plurality of successive periods. The table of FIG. 6 is exemplary.

Figure 6:
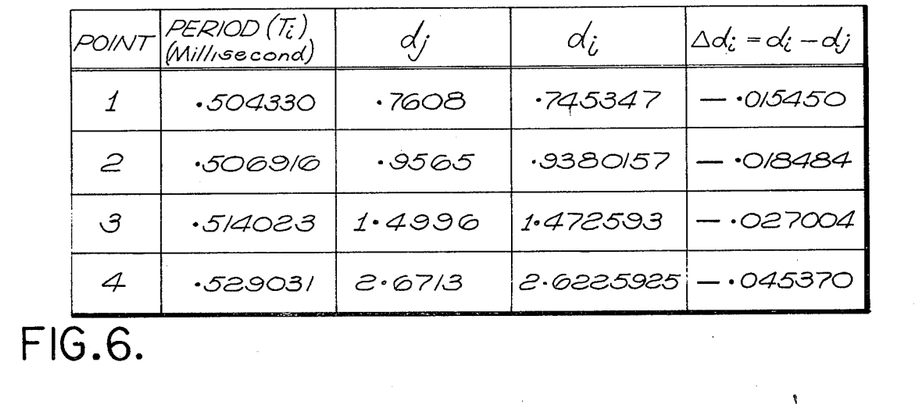
FIGS. 6, 7 and 8 are tables illustrating typical values for construction of the present invention.

Once the data of FIG. 6 is known ($\Delta d_i$ is calculated by subtraction, of course — $T_i$ is the period in both gases), $\Delta T_i$ is calculated from one of the equations (14) and (15) for each of the points 1, 2, 3 and 4 in FIG. 6, although any number of points may be used. The term $\Delta T_i$, in microseconds, so calculated from the data of FIG. 6 is $-207.89$, $-247.45$, $-356.52$ and $-58.20$ for the points 1, 2, 3 and 4, respectively, in FIG. 6.

Figure 7:
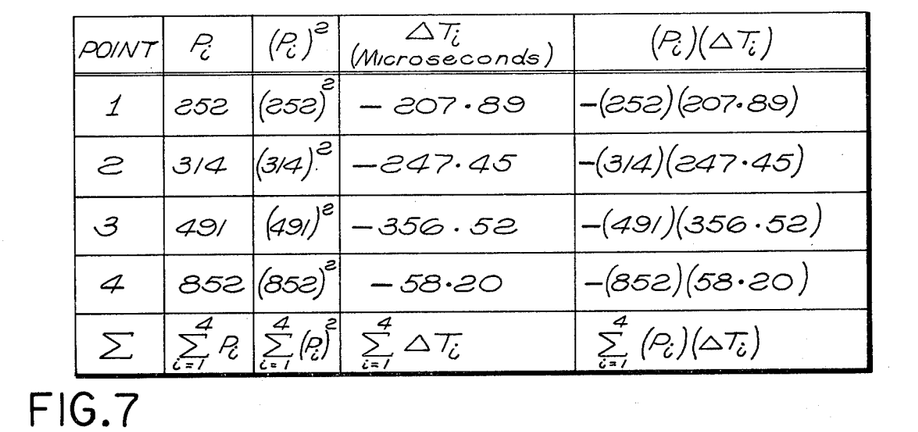

From the data given hereinbefore and in FIG. 6, $\Delta T_i$ is preferably curve fit to $P_i$ by finding $K_a$ and $K_b$ of equation (15) by the LSM as shown in FIG. 7.

From FIG. 7, $K_a$ and $K_b$ of equation (16) may be determined by solving the following simultaneous equations (18) and (19) therefor.

$$4K_a + K_b \sum_{i=1}^{4} P_i = \sum_{i=1}^{4} \Delta T_i \qquad (18)$$

$$K_a \sum_{i=1}^{4} P_i + K_b \sum_{i=1}^{4} (P_i)^2 = \sum_{i=1}^{4} (P_i)(\Delta T_i) \qquad (19)$$

The zero and span adjustments of any conventional pressure sensor may be employed to determine $k_a$ and $k_b$, respectively. Pressure sensor 50 in FIG. 2 may be entirely conventional. Pressure sensor 50 provides a D.C. output voltage E18 (see FIG. 9) directly proportional to $|\Delta T_i|$. For the table of FIG. 7, with $\Delta T_i$ in microseconds $$\Delta T_i = -[51.229 + 0.6228 P_i] \qquad 20$$

Figure 8:
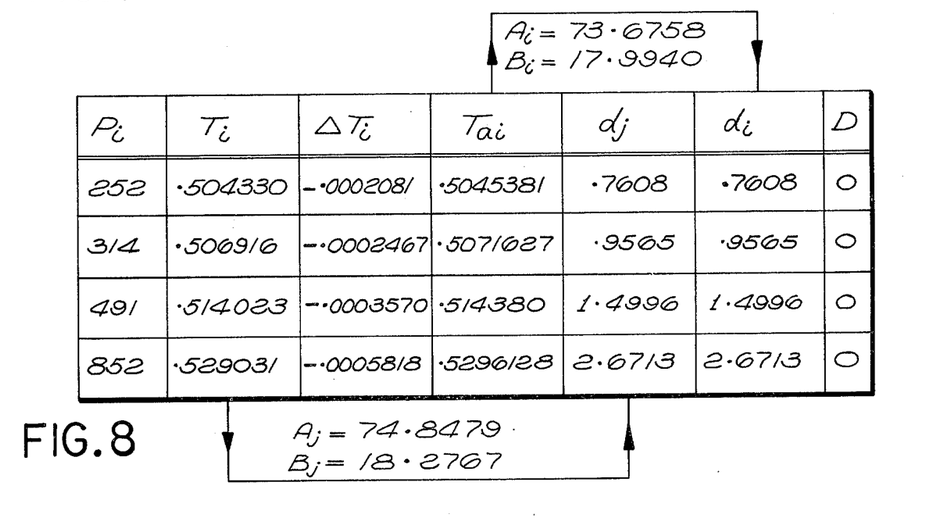

The table of FIG. 8 is the proof of the combined calibrations. Note columns $d_j$ and $d_i = f(T_{ai})$ are identical, where $$d_j = A_j T_j^2 - B_j \qquad 21$$

and $$d_i = A_i T_{ai}^2 - B_i \qquad 22$$

and $$T_{ai} = T_i - \Delta T_i \qquad 23$$

The term D in FIG. 8 is deviation. Note in FIG. 8 that $d_j$ and $d_i$ are identical for all four pressures.

In FIG. 4, integrator 52 is started on a ramp E19 in waveform E14 of FIG. 9 at junction 57 in FIG. 4 at the beginning of the leading and trailing edges of pulses appearing at junction 398 in FIG. 2. The waveform appearing at input lead 66 in FIG. 4 and at junction 398 in FIG. 2 is shown at E5 in FIG. 11 and at E56 twice in FIG. 9. The waveforms E'56 in FIG. 9 are enlarged over E5 in FIG. 11 to demonstrate better how $\Delta T_i$ is used, $\Delta T_i$ being very small.

In FIGS. 4, 9 and 11, flip flop 71 is set at the leading and trailing edges of E5 by one shots 63 and 64. One shots 63 and 64 also reset integrator 52 by closing switch 55 each time flip flop 71 is set. The 1 output of flip flop 71 is connected to input switch 59 and thereby closes the same when flip flop 71 is set. Ramp E19, which is a portion of E14 in FIG. 9, then begins. Ramp E19 then terminates at time $t1$ when the ramp voltage E19 at junction 57 in FIG. 4 becomes equal to the D.C. output voltage of pressure sensor 50 (FIG. 2) received over lead 69 (FIG. 4). Junction 57 in FIG. 4 then remains at potential E18 (FIG. 9) because one shot 70'(-FIG. 4) resets flip flop 71 and the 1 output thereof opens input switch 59 in FIG. 4.

The waveforms E'89 or E''89 are the accurate forms of E8 and E9 in FIG. 11, but only during nitrogen use. Pulses are added during $t1$ directly proportional to $-\Delta T_i$ in E89. Pulses are subtracted directly proportional to $-\Delta T_i$ in E''89 ($\Delta T_i$ positive).

In FIG. 9, E15 is the output of one shot 70' in the pick off 42 of FIG. 4. The voltages E16 and E17 in FIG. 4 are the 1 and 0 outputs of flip flop 71 and of pick off 42, the former being included in the latter in FIG. 4.

OPERATION OF THE DIGITAL FUNCTION GENERATOR 30 OF FIGS. 1 AND 2

Loop circuit output lead 34 in FIG. 1 impresses a square wave on digital function generator input lead 393 shown in FIGS. 1 and 2, the said square wave having a mark-to-space ratio of unity. Density indicated at 27' in FIG. 2 is a function of the period of the said square wave in accordance with equation (2). The same is true of square waves E5 and E6 shown in FIG. 11 which appear at junctions 398 and 403 in FIG. 2, respectively.

The output of NAND gates 399 and 400 is E9 and E8, respectively, when switches 46 and 46' are open. In this case, if operators 361 in FIG. 3 are set to $A_j$ and matrix $A'$ in FIG. 10 is set to $B_j$, indicator 27' in FIG. 2 will read methane density. Computer 10' in FIG. 2 produces a number of output pulses to computer 354 directly proportional to the number of pulses in a group of E8 or E9 in FIG. 11. Since density does not necessarily change rapidly, the pulses in the first grup in E8 may be identical in number to those in the first group of E9.

Offset digital computer 354 shown in FIG. 2 simply subtracts $B_j$ from the output of square law digital computer 10'. The output of the latter is $A_j T_j^2$. The methane or other gas of use calibration may be easily checked against measured densities in this way by both the manufacturer and the customer. For both to check the nitrogen calibration against measured values, switches 46 and 46' are closed (in the case of another gas or gas mixture where $\Delta T_i$ is positive switch 46' is closed, but arm 47 of switch 46 is grounded on contact 49 thereof). Pulses are then added or not from the outputs of NAND gates 399 and 400 in direct proportion to $-\Delta T_i$ or $+\Delta T_i$, respectively, and in direct proportion to the time during which the 1 output of pick off 42 is high. This results in a period subtraction when $\Delta T_i$ is positive. During this period NAND gates 399 and 400 produce no pulses whatsoever, and pulses are alternately added or not in OR gates 40 and 343 if switch 46 is closed (as shown) or open (pole 47 grounded), respectively.

The period $\Delta T_i$ may sometimes partly or always be determined by adjustment at knob 58' of source 58 in FIG. 4 which determines the slope of E19 in FIG. 9. In FIG. 9 $t1$ is directly proportional to the D.C. output voltage of pressure sensor 50.

The output of one shot 342 in FIG. 2 merely resets divider 37' shown in FIG. 3 and the input from inverter 43 to NAND gate 352 disables the latter during that reset.

All the other structures in FIG. 2 that operate computer 354 are identical to or equivalent to those disclosed in P5, P6 and P7 and operate in exactly the same way as do computers 10' and 354, and indicator 27'. The only differences betwen P5, P6 and P7, and the operators of computer 354 are that an AND gate is disclosed in P5, P6 and P7 for each of the NAND gates 44 and 45, and inverters 36' and 39' are omitted.

The constants A and B may be determined empirically by placing the densitometer probe 34' in FIG. 1 in two different fluids of two different known densities each time measuring $T$. The constants A and B may then be calculated from two simultaneous equations per patent P1. However, the LSM is preferred.

Something about certain structures disclosed herein is discussed in the material immediately following. The importance of some of this discussion may be apparent only from subsequent explanations.

A main storage register $D'$ is illustrated in FIG. 10. As will be described, a predetermined number $B''$ is entered in storage register $D'$ is a counter 23' periodically.

A logic circuit is provided at 13'. Logic circuit 13' has an input from square law computer 10' through switch 32'.

In FIG. 10, the said predetermined number $B''$ is periodically entered in storage register $D'$, as stated previously. The magnitude of the predetermined number $B''$ may be selected or changed by operating binary or binary coded decimal (BCD) switches which are located in a switch matrix $A'$. The switches in matrix $A'$ are either connected from a positive potential or ground. The outputs of the switches are sampled and impressed upon storage register $D'0$ periodically. A gating pulse (E13 in FIG. 11) is impressed upon a gating circuit $B'$ for this purpose from inverter 39'.

Gating circuit $B'$ is connected from matrix $A'$ to an OR gate matrix $C'$. The output of OR gate matrix $C'$ is then impressed upon storage register $D'$.

Once the said predetermined number $B''$ has been entered into storage register $D'$, logic circuit 13' then controls the register $D'$ to count up or down depending upon whether the signs of A and B are the same or different, switch 32' in FIG. 10 being placed in the one or the other of corresponding positions thereof, respectively, on this account. The output of logic circuit 13' is, thus, impressed upon storage register $D'$ through OR gate matrix $C'$. Logic circuit 13' receives pulses to count from switch 32'. Logic circuit 13' receives other inputs from storage register $D'$.

From the foregoing, it will be appreciated that matrix C' with logic circuit 13' and storage register D' form either a count up-count down counter depending upon in which position switch 32' lies. This counter may be entirely conventional, if desired.

The output of storage register D' is also sampled periodically by a gating circuit 24' which may be of the same type as gating circuit B'. Gating circuit 24' receives pulses from inverter 36' in FIG. 2 to cause it to sample the output of register D'. The output of gating circuit 24' is impressed upon a storage register 26'. The output of the storage register 26' is impressed upon indicator 27'.

If desired, indicator 27' may be a binary indicator or a BCD indicator.

All of the structures D', 13', A', B', C', 24', 26' and 27' may be entirely conventional or may or may not be identical to the corresponding structures disclosed in P8.

Alternatively, indicator 27' may simply be a row of lamps each connected from the 1 output of each of the flip flops in storage register 26'.

Pulses are supplied from inverter 36' to gating circuit 24'.

The purpose of the switch matrix A' is to set, periodically, the flip flops in storage register D' to selected states.

Switch matrix A' may have one double-pole, double-throw switch for each bit or flip flop in register D'. Gating circuit B' may have an AND gate for the set 1 and set 0 inputs to each bit or flip flop in register D'. The OR gate matrix C' may have an OR gate for the set 1 and set 0 inputs of each bit in register D'.

The same outputs of the bits of register D' are connected both to logic circuit 13' and to gating circuit 24'.

The square wave at junction 406 in FIG. 2 is illustrated at E1 in FIG. 11.

The square wave which appears at the output of inverter 415 in FIG. 2 is illustrated at E2 in FIG. 11.

The square wave which appears at junction 407 in FIG. 2 is illustrated at E3 in FIG. 11.

The square wave which appears at the output of inverter 418 in FIG. 2 is illustrated at E4 in FIG. 11.

The square wave which appears at the terminal junction 398 in FIG. 2 is illustrated at E5 in FIG. 11.

The square wave which appears at junction 403 in FIG. 2 is illustrated at E6 in FIG. 11.

The output of burst oscillator 30' is illustrated at E7 in FIG. 11.

The output of NAND gate 400 (methane only in the following) in FIG. 2 is illustrated at E8 in FIG. 11.

The output of NAND gate 399 in FIG. 2 is illustrated at E9 in FIG. 11.

The output of differentiator 416 in FIG. 2 is illustrated at E10 in FIG. 11.

The output of one shot 417 shown in FIG. 2 is illustrated at E11 in FIG. 11.

The output of inverter 36' shown in FIG. 2 is illustrated at E12 in FIG. 11.

The output of inverter 39' shown in FIG. 20 is illustrated at E13 in FIG. 11.

The phrase "utilization means," as used herein and in the claims, is hereby defined to include, but not be limited to, an indicator, a process controller, or otherwise.

Although a symbol has been used consistently in the drawings to represent OR gates, it is to be understood that the symbol includes, but is not limited to, a wire OR gate. Thus, one or more or all of the symbols employed herein to represent an OR gate may or may not be a wire OR gate, as desired.

The phase "OR gate," as used herein and in the claims, is hereby defined to include a NOR gate with or without an inverter, as may be necessary or desirable.

The phrase "NAND gate," as used herein and in the claims, is hereby defined to include an AND gate with or without an inverter, as may be necessary or desirable.

In FIG. 1, digital function generator 30, having input lead 393, may have the said input lead 393 connected from loop circuit output lead 33 or from any other appropriate conductor in loop circuit 29.

As indicated hereinbefore, binary or binary decimal systems may sometimes be used entirely in part, not at all, as shown or to a greater or less extent than that disclosed herein.

The word "densitometer," as used herein and in the claims, is hereby defined to include, but not be limited to, that shown with or without (1) utilization means, (2) a process controller, (3) a density or specific gravity indicator, or (4) otherwise.

The phrase "specific gravity," as used herein and in the claims, is hereby defined as the equivalent of density and as the ratio of the density of a sample fluid to the density of a reference fluid, the reference fluid being air or any other fluid at a reference temperature and pressure.

If it has not been made abundantly clear hereinbefore, no pressure sensor to pipeline connection need to made during density measurement or otherwise of methane or the gas of interest as opposed to nitrogen or the gas of calibration.

The word "gas" is hereby defined for use herein and in the claims to mean either a pure or relatively pure gas such as pure nitrogen gas or pure methane gas, or a mixture of two or more gases.

The word "fluid" as used herein and in the claims is hereby defined to include either one elemental gas or a mixture of gases, but to exclude all liquids.

What is claimed is:

1. A densitometer comprising: a probe assembly having a structure to be vibrated while immersed in both a calibration fluid $i$ and a fluid of use $j$ different from said fluid $i$; a loop circuit connected from and to said probe assembly forming an electromechanical oscillator therewith, said loop circuit having an output lead and first means for producing a rectangular wave thereon of a predetermined frequency directly proportional to the vibrational frequency of said structure, said predetermined frequency being the reciprocal of the period $T_i$ for a density $d_i$ of said fluid $i$ in a first equation, $$d_i = A_i T_i^2 - B_i$$

where $A_i$ and $B_1$ are constants, said predetermined frequency being the reciprocal of the period $T_j$ for a density $d_j$ of said fluid $j$ in a second equation, $$d_j = A_j T_j^2 - B_j$$

where $A_j$ and $B_j$ are constants, said first and second equations accurately defining said densities $d_i$ and $d_j$ as functions of said periods $T_i$ and $T_j$, respectively; second means actuable to produce an output signal $\Delta T_i$ which is a function of the pressure of said fluid $i$; and computer means for solving a third equation, $$d_j = A_i(T_i - \Delta T_i)^2 - B_i$$

for $d_j$ as a function of $T_i$ and $\Delta T_i$ and to produce an output signal $d_j$ which is effectively the same as said $d_j$ term in said second equation.

2. The invention as defined in claim 1, wherein said second means includes a pressure sensor for producing an output signal directly proportional to $\Delta T_i$, said computer means including switch means connected from said pressure sensor selectively actuable to render $$\Delta T_i = 0$$

3. The invention as defined in claim 2, wherein $\Delta T_i$ is a linear function of the pressure of said fluid $i$.

4. The invention as defined in claim 1, wherein $\Delta T_i$ is a linear function of the pressure of said fluid $i$.

* * * * *